United States Patent [19]

Bowen

[11] Patent Number: 5,057,018

[45] Date of Patent: * Oct. 15, 1991

[54] MICROCRYSTALLINE INSERTS FOR MEGAFILLED COMPOSITE DENTAL RESTORATIONS

[75] Inventor: Rafael L. Bowen, Gaithersburg, Md.

[73] Assignee: American Dental Association - Health Foundation, Gaithersburg, Md.

[*] Notice: The portion of the term of this patent subsequent to May 17, 2005 has been disclaimed.

[21] Appl. No.: 561,357

[22] Filed: Aug. 1, 1990

Related U.S. Application Data

[63] Continuation of Ser. No. 194,413, May 13, 1988, abandoned, which is a continuation-in-part of Ser. No. 862,706, May 13, 1986, Pat. No. 4,744,759.

[51] Int. Cl.$^5$ .................... A61C 5/04; A61K 6/02
[52] U.S. Cl. .................... 433/228.1; 106/35; 501/4; 501/7; 501/8; 501/63; 501/64; 501/68; 501/69; 501/73; 523/116
[58] Field of Search .................... 433/215, 216, 228.1; 523/116; 106/35; 501/4, 7, 8, 63, 64, 68, 69, 73

[56] References Cited

U.S. PATENT DOCUMENTS

| | | |
|---|---|---|
| 139,012 | 5/1873 | Mack . |
| 764,871 | 7/1904 | Sparks . |
| 1,063,376 | 6/1913 | Nies . |
| 2,538,486 | 1/1951 | Tofflemire .................... 32/15 |
| 2,644,232 | 7/1953 | Roubian .................... 32/15 |
| 3,314,420 | 4/1967 | Smith et al. .................... 128/92 |
| 3,801,344 | 4/1974 | Deitz .................... 501/8 |
| 3,973,972 | 8/1976 | Muller .................... 501/4 |
| 3,975,203 | 8/1976 | Dietz .................... 501/8 |
| 4,001,939 | 1/1977 | Gross .................... 32/15 |
| 4,097,935 | 7/1978 | Jarcho .................... 3/1.9 |
| 4,189,325 | 2/1980 | Barrett et al. .................... 501/7 |
| 4,744,759 | 5/1988 | Bowen .................... 433/288.1 |
| 4,747,876 | 5/1988 | Hakamatsuka et al. .................... 501/7 |
| 4,799,887 | 1/1989 | Hakamatsuka et al. .................... 501/7 |
| 4,814,297 | 3/1989 | Beall et al. .................... 501/7 |

FOREIGN PATENT DOCUMENTS 16126 of 1903 United Kingdom .

Primary Examiner—Paul Lieberman
Assistant Examiner—William S. Parks
Attorney, Agent, or Firm—Allegretti & Witcoff, Ltd.

[57] ABSTRACT

Means to decrease the effects of polymerization shrinkage, increase stiffness, decrease the coefficient of thermal expansion to a greater extent than previously possible, and improve the durability of composite restorations by use of improved microcrystalline glass inserts. Shaped pieces of assorted sizes within the range of one-half to 10 millimeters are heat treated to produce microcrystallinity in which the crystalline phases, such as for example stuffed beta quartz, beta-eucryptite, beta-spodumene solid solutions, and keatite and/or other phases, give the microcrystalline glass pieces exceptionally low coefficients of thermal expansion and other desirable properties. Compositions and heat treatment conditions are given to provide the insert pieces with the desired translucencies/opacities, colors, and shades, to match a range of those properties found in teeth. Treatment of the inserts with an organofunctional silane with or without an additional resin coating provides for chemical bonding with composite resins. Cavities in teeth are partially filled with unhardened composite material, and microcrystalline glass inserts of appropriate size, shape and appearance are pressed into the cavity so that the insert constitutes as much as possible of the finished restoration. The composite containing the insert is polymerized either by light, chemical, or combined cure mechanisms, and contoured and polished.

7 Claims, No Drawings

MICROCRYSTALLINE INSERTS FOR MEGAFILLED COMPOSITE DENTAL RESTORATIONS

This invention was supported in part by U.S. Public Health Service Research Grant DE-05129 to the American Dental Association Health Foundation from the National Institutes of Health-National Institute for Dental Research, Bethesda, Md.

This application is a continuation of application Ser. No. 194,413, filed May 13, 1988, now abandonded, which is in turn a continuation-in-part of Ser. No. 862,706, filed May 13, 1986, now U.S. Pat. No. 4,744,759.

BACKGROUND OF THE INVENTION

This invention relates to the field of dental composite resin restorations. Composite dental restorative materials are described in U.S. Pat. No. 3,066,112, issued in November 1962. Current practice in filling cavities with cosmetically appealing compositions involves the use of resins mixed relatively homogeneously with a very finely divided or colloidal filler. There are a number of undesirable characteristics of present composite materials and restorations made from them. Some of these include the problem of polymerization shrinkage, high coefficient of thermal expansion relative to the tooth crown, and low stiffness (modulus of elasticity). The shrinkage tends to allow contraction gaps and microleakage around the restorations. The differential coefficient of thermal expansion tends to promote the microleakage and staining of the margins of the restoration. The low stiffness of the restoration results in loss of support of remaining tooth structures.

Composite resin dental materials of this type are, for example, described in U.S. Pat. No. 4,215,033, issued July 29, 1980, and in Bowen et al., "Semiporous Reinforcing Fillers For Composite Resins: I. Preparation of Provisional Glass Formulations," 55 *J. Dent. Res.* 738-47 (1976), and Bowen et al., "Semiporous Reinforcing Fillers For Composite Resins: II. Heat Treatments and Etching Characteristics," 55 *J. Dent. Res.* 748-56 (1976). See also, Bowen et al., "Theory of Polymer Composites," *International Symposium on Posterior Composite Resin Dental Restorative Materials,* 95-107 (Peter Szulc Pub., The Netherlands, 1985), and references cited in each of the above articles and patent.

U.S. Pat. No. 4,215,033 in particular describes a transparent glass filler material in which the glass is separated into two interconnected vitreous phases which after crushing and ball milling to a very fine powder, is acid etched to produce a porous surface layer. Preferred glass compositions disclosed in this patent include a mixture of silicon dioxide, boron oxide, aluminum oxide and strontium oxide, with one or more from the group of calcium oxide, zinc oxide, stannic oxide, and ziroconium oxide as optional modifying ingredients. The transparent inorganic glass particles of microscopic size are silane treated and then combined with an organic resin to provide an improved composite dental material.

SUMMARY OF THE INVENTION

The present invention provides large esthetic inserts for direct-filling dental restorations in the form of relatively large individual pieces sized and shaped to fill a cavity as nearly as possible with a single piece per cavity restored in a given tooth surface, and designed to be cemented into place in the cavity with a macrofilled, hybrid, or unfilled resin.

It is an object of this invention to reduce the hardening shrinkage previously associated with the use of composite materials in restorations.

It is a further object of the invention to lower (improve) the coefficient of thermal expansion of the restoration, more than has been previously possible, by the use of insert materials having extremely low or even negative coefficients of thermal expansion.

An additional object of the invention is to increase the stiffness (modulus of elasticity) of composite fillings by providing new megafiller insert materials with higher stiffness than previously available.

Another object of the invention is to maintain x-ray opacity comparable to that of the enamel of teeth in the restoration comprised of insert(s) and composite filling material, while providing the visual translucency necessary for esthetic appearance of the restoration, and to allow the photocuring light to penetrate through both the composite and the insert to harden the composite in the deeper aspects of the restoration.

A very important object of the instant invention is the improvement in color characteristics of insert materials so that they will have the appearance of natural teeth, and provision of a means to effect a darkening of the shade of the insert into the range of natural tooth shades.

Another object of the invention is to provide a simplified silane treatment of inserts for use in dental composite restorations.

The megafiller inserts are not designed to fit the cavity preparations exactly, as do precision castings which are custom-made in dentistry. Custom-made precision castings are very expensive relative to "direct-filling materials". Direct-filling materials are those with which a dentist can completely restore a dental cavity in a single appointment and procedure. The present invention provides a means to make mass-produced inserts which serve many of the beneficial functions of cast or custom-formed porcelain inlays, but with much less expense in their fabrication and utilization. The present method allows the preparation and selection of improved inserts which approximately fill a given dental cavity preparation by selection from a group or set of inserts. The dentist can select an insert which will fit the cavity preparation partly, the rest of the cavity being filled with the composite restorative material.

These inserts can be of metal compositions for use in those areas of the mouth where esthetics is not a consideration, or of glass, microcrystalline glass, ceramic, or porcelain materials where esthetics in the final restoration is important because the tooth is occasionally visible.

The most preferred embodiment of the present invention utilizes special, improved, glass compositions which can be heat treated to form microcrystalline glasses with properties more nearly ideal for use as inserts for composite resin restorations. These contain silicon dioxide and at least one other oxide selected from the group consisting of aluminum oxide, lithium oxide, zinc oxide, magnesium oxide, titanium oxide, zirconium oxide and phosphorus oxide. More preferably they contain silicon dioxide; aluminum oxide, and at least one oxide from the group consisting of zinc oxide, magnesium oxide, lithium oxide, and/or other modifier oxides (optionally); one or more oxides from the group consisting of zirconium oxide, titanium oxide, phosphorous oxide, and/or other oxides to facilitate phase separation and nucleation of microcrystals of the desired characteristics; iron oxide, iron oxalate, cerium oxide in titania-containing glasses, or other compounds, elemental sulfur or a compound containing sulfur, optionally, and/or other elements or compounds to provide the desirable yellow-amber-brownish tint to the microcrystalline insert for color matching with teeth; and metallic aluminum powder, sugar, and/or other carbonaceous compounds to obtain the desired reducing conditions for the formation of the color-forming agents within the microcrystalline glass insert material. Exposure of the microcrystalline glass inserts (after production but before placement in the composite restoration) to ionizing radiation, in order to obtain the desired shade for tooth matching, is an option.

These preferred glasses may contain, for example, ranges such as: silica, 33 to 80 mol %; aluminum oxide, 1 to 30 %; lithium oxide, 0 to 20 mol %; zinc oxide, 0 to 25 mol %; magnesium oxide, 0 to 20 mol %; titanium oxide, 0 to 25 mol %; zirconium oxide, 0 to 6 mol %; phosphorous oxide, 0 to 10 mol %; iron equivalent to 0 to 5 mol % ferric oxide; sulfur in some form equal to 0 to 5 mol %; cerium oxide, 0 to 5 mol %, and other modifiers and oxides such as calcium, strontium, tin, niobium, tantalum, tungsten and others, and agents for producing a reducing effect during the melt and microcrystalline glass formation such as various carbonaceous materials, metallic aluminum, oxalates, and/or the metallic forms of some of the aforementioned metal oxides. One of the most preferred compositions in mol % is silicon dioxide, 58; aluminum oxide, 21; lithium oxide, 6; zinc oxide, 5; magnesium oxide, 6; and titanium oxide, 4 mol %. Another contains 60, 18, 6, 6, 6 mol % of the same oxides respectively and 4 mol % zirconium oxide in place of titanium oxide.

The most preferred composition is similar to the last one listed, but with the addition of trace amounts of elements and oxides which give a slight yellowish brown tint to the finished insert such as to match in appearance the color and shade of the natural teeth.

In the most preferred embodiment, the mix is melted to form a liquid. The liquid is mixed to homogenize it, and the molten glass is then poured in between water-cooled rollers which are synchronized and shaped so as to form objects of assorted sizes and shapes appropriate for partially filling typical dental cavities. The inserts can also be prepared by a pressing method, by dry gauging, and by other methods known to the art of glass object forming. These shaped pieces are then heat-treated to nucleate and crystalline the microcrystalline glass objects and, optionally, exposed to ionizing radiation to produce shades matching human teeth. The heat-treated pieces can be selected and sorted for size and type of insert. Surface roughening of the inserts by etching with strong acid or base solutions is optional but is not necessary.

In batches, the insert pieces are treated with an organofunctional silane coupling agent. The silane treatment of microcrystalline glass inserts can be accomplished as follows: the pieces are weighed in a closable glass container. About 0.75% (by wt of inserts) of Union Carbide A-174 (3-methacryloxypropyltrismethoxy silane) is mixed with enough cyclohexane so that the solution will cover the pieces in the container. About 2% (by wt of inserts) of n-propylamine is mixed with a little cyclohexane. The silane solution and then the n-propylamine solution are added to the insert pieces in the container. The covered container is gently swirled occasionally (four times) during a 1½ hour soak period. The cap is then removed and the solvent left to evaporate off. Alternatively, the organofunctional silane coupling agent is combined with a dimethacrylate resin which is partially or completely polymerized on the surface.

The open container is placed in a vacuum oven at 110° to 120° C. for one hour, followed by three rinses with cyclohexane to remove residual n-propylamine and soluble silane by-products. The insert pieces are dried for about one hour and then stored in a covered container. The insert pieces can then be optionally coated with a polymerizing resin layer and packaged for sale to dentists in compartments segregated according to suitable sizes and shapes from which the dentist can select an insert for a given dental cavity preparation.

The resulting insert pieces are, as a further aspect of the invention, employed in a method for repairing cavities in teeth comprising partially filling the cavities with unhardened composite materials, pressing an insert piece prepared as described above into the composite material, removing excess extruded composite material, curing (hardening) the composite material, and contouring the surface of the composite and/or insert (if it is exposed to the final restoration surface) to the appropriate contour. The invention further contemplates a dental restoration comprising the product of the methods described herein.

The volume percent crystallization of the glasses described herein may be varied from 0 to approximately 100%, depending on the composition, heat treatment, and properties desired, to facilitate economical improved composite restorations by the incorporation of prefabricated inserts produced by mass-production methods.

DESCRIPTION OF PREFERRED EMBODIMENTS

The complete disclosure of U.S. Pat. No. 4,744,759, is expressly incorporated herein by reference.

Since the filing of that application, it has been discovered that the heat treatment of inserts during phase separation and/or microcrystallization yields a silica-rich outer surface which is especially suitable for effective treatment with an organofunctional silane chemical bonding agent. This silane provides excellent adhesive bonding between the composite resin and the glass insert surface. With the microcrystalline glasses of the present invention, the silane treatment is effective with or without prior etching of the insert surface. The microcrystallinity of inserts of the present invention allow for etching by substantially the same procedures as described in U.S. Pat. No. 4,744,759 to obtain a microscopically rough outer surface to provide increased surface area for silane promoted adhesive bonding with the resin of the composite material. In the most preferred embodiment, the freshly formed or cleaned and dried surface of the microcrystalline glass insert is treated with the silane (3-methacryloxypropyltrismethoxy silane).

The forming and shaping of the microcrystalline glasses of the present invention can be accomplished by the same methods as described in U.S. Pat. No. 4,744,759 or by other methods well known to the art of glass making while the microcrystalline glass formulations are still in the amorphous glassy condition before heat treatment to develop the microcrystallinity of the insert.

One optional method of obtaining megafiller pieces is to pour the melt into water, segregate the pieces into size classifications, heat treat the pieces, and either before or after heat treatment, tumble batches of these together with grit (slurries of coarse to fine abrasive powders, such as silicon carbide and others) in a rotating drum, barrel, or jar, wash the rounded megafiller pieces free of grit on appropriate sieves, and then proceed with the silane treatment of the batches of megafiller pieces.

The most preferred embodiment of the present invention incorporates microcrystalline glass compositions having the following characteristics: very low (approximately 0) coefficients of thermal expansion; visual translucency (and also visual opacity) which approximates that of tooth enamel; colors and shades closely resembling those of tooth crowns and esthetic composite materials; increased stiffness (modulus of elasticity) and strength; ease of fabrication; and relatively low cost of ingredients, distribution, and application, relative to state-of-the-art porcelain and ceramic custom-made precision inlays.

A low coefficient of thermal expansion is important to offset the high coefficient of thermal expansion of the composite portion of the restoration relative to the tooth crown. Contemporary composites have coefficients of thermal expansion approximately 3 to 5 times higher than that of the tooth crown, and the insert with very low thermal expansion and contraction upon heating and cooling by foods and beverages will yield a restoration with overall thermal characteristics much closer to the tooth crown.

Translucency is important because of the desirability of transmittance of light to the underlying composite material during the curing of the composite by photoactive mechanisms, and for esthetics of the restoration.

The colors and shades of the insert are important because the composite material as well as the tooth structure is translucent, and colors or shades that do not match the tooth will "shine through" and yield a restoration that does not match the appearance of the natural tooth.

The stiffness of composite restorations is considerably lower than that of the tooth crown and the incorporation of a highly stiff, rigid insert will increase the overall rigidity of the restoration, thereby giving greater support to the remaining tooth structure. The microcrystalline glasses of the present invention can be fabricated and shaped easily while still in the glassy condition at the desired viscosity and will not lose this shape during the heat treatment to produce the microcrystallinity.

The ingredients are readily available, relatively inexpensive, require only ordinary facilities for heat treatment, allow for convenient distribution to dentists, and allow for improved composite restorations at minimal additional expense.

Megafiller inserts, typically 0.5 to 10 millimeters in size, should be selected to fit the size and shape of the cavity as nearly as possible. The cavity is then partially filled. Microcrystalline glass inserts are fitted into cavities of any appropriate kind, keeping in mind the advantages and limitations of improved composite restorations containing these inserts. These prefabricated microcrystalline glass inserts function as extremely large "megafillers" and reduce the mass of composite resin to be polymerized. The inserts can be selected with the help of a gauge, to simplify the selection of the best insert for a given cavity.

The glass inserts of the most preferred embodiments of this invention are light-conducting and scatter light only sufficiently to match the esthetics of dental enamel such that the deep portions of the light-cured composite resin are also thoroughly polymerized. For more opaque inserts, composite restorations, and teeth, a composite of the chemical curing (self-curing) type should be used, or, optionally, a composite that has a dual-cure system which allows it to harden both chemically without light and more rapidly under the influence of a curing light may be used. Composites of these types are currently available to the profession. Because there is only a small mass of composite resin to be polymerized, the vectors of shrinkage, which are directed toward the insert, will not negatively influence the marginal seal, especially if the resin has adhesive bonding capacity as provided for in prior patents (U.S. Pat. Nos. 4,514,527, 4,521,550, 4,588,756 and 4,659,751).

In the utilization of this invention, the cavity is partially filled with soft composite resin (the cavity walls and matrix, if any, being covered), and the microcrystalline glass insert selected is forced into the unset composite and can optionally be held under pressure during curing of the composite resin. The insert can be completely embedded and covered by the composite resin in the final restoration, or, optionally, the insert can comprise a minimal or maximum amount of the finished surface of the restoration. One of the advantages of the microcrystalline glass materials of the type described herein is that they can be polished to a shiny surface matching that of natural teeth and microfilled composite resins. Preferably, excess unset resin is removed from around the insert before the composite is hardened in cases where the insert is larger than the size of the final (finished) restoration. The cured composite and insert can be contoured by the use of high-speed rotary diamond instruments with water-cooling and high-volume evacuation. They can then be finished to a high luster by methods currently used in dentistry.

Examples of glass formulations for the preparation of microcrystalline glass inserts that fall within the scope of the present invention are given in Table 1. Glasses from these compositions were melted in the conventional manner and poured into small molds and into water for quenching, and some portions were quenched in air, forming strings or rods of their glass. The larger castings were annealed to facilitate specimens being cut from them for observations of differential thermal analysis and coefficients of thermal expansion. Water-quenched and air-quenched strings were selected in size ranges that would be suitable for inserts in composite restorations in human teeth. These specimens were heat treated at about 750° C. for one hour, 800° C. for one hour, 850° C. for two hours, and 900° C. for two hours in sequence, aliquot samples being taken before heat treatment and at the end of each of the foregoing steps of heat treatment.

EXAMPLE 1

One of the most preferred formulations is composition 7 (K-2783) in Table 1. The glass after quenching was clear with a very light straw color. This color increased gradually with the sequence of heat treatments to a light amber translucent microcrystalline glass product having very slight opacity and a light tooth color after the 850° C. treatment for two hours and a dark tooth color with remaining translucency after 900° C. at two hours additionally. Microcrystalline glass inserts of this stuffed beta quartz composition would not require ionizing radiation to give darker shades to match tooth appearance.

EXAMPLE 2

Another preferred embodiment of the present invention is the formulation shown in Table 1 and designated Composition #5 (K-2780). This composition melted to a clear colorless glass which could be quenched or cast and annealed with no visible phase separation and which upon heat treating according to the aforesaid sequence yielded pratically colorless translucent microcrystalline inserts, the light-scattering opacity of which increased gradually to the end of the 850° C. (two hours) treatment and remained the same or decreased slightly after 900° C. (two hours). Inserts of this type would be useful for obtaining maximum degree of cure in the base of large restorations when light cure composite resin is used. Darker shades can be obtained by exposure to ionizing radiation such as radiation obtained from radioactive cobalt sources and other sources. Such darkening by exposure to ionizing radiation is obtained after heat treatment but before silane treatment of the microcrystalline glass objects.

EXAMPLE 3

The melt with composition #8 (K-2785) in Table 1 gave a clear light yellow glass which showed no visually perceptible change after one hour at 800° C., but which was more opaque to visible light after two hours at 850° C. than most teeth or composite restorative materials. This formulation would therefore require careful heat treatment within the range of 800° to 850° C. for a time between one and two hours to obtain an appearance matching teeth and composite restorations. It might also be necessary to add a trace of cerium oxide, iron, and/or sulfur to obtain a more yellowish hue resembling tooth coloration.

EXAMPLE 4

The composition #6 (K-2781) of Table 1 showed a tendency toward opacification during slow cooling as in the cast block and therefore required rapid quenching to obtain a clear light amber glass. However, when these clear rapidly quenched samples were heat treated according to the stated thermal sequence, there was a gradual and esthetically desirable increase in opacity with the maintenance of a tooth coloration.

Samples exposed to ionizing radiation became darker in shade in proportion to the total radiation exposure. This is a means of adjusting the shade of microcrystalline glass, ceramic, and vitreous phase separated glass inserts for dental composite restorations to varying degrees to match the shade of the composite and tooth crowns. A suitable source of ionizing radiation is cobalt 60 and/or x-radiation of high energy and flux density.

Ordinary dental diagnostic x-ray procedures will not cause perceptible change in the shade of these materials because of relatively low energy and very low flux. However, it is important that these inserts have x-ray opacity comparable to tooth enamel. Composition #4 (K-2769) was compared with an equal thickness of a tooth sample prepared from an extracted tooth using dental diagnostic x-ray film. This formulation was more x-ray opaque than the enamel of the tooth, and therefore, more than adequately x-ray opaque for diagnostic clinical evaluations. The dental x-ray opacity is attributed mainly to the zinc or zirconium oxide content and to the other elements to a lesser extent. The compositions #1 (K-2681), #2 (K-2715), and #3 (K-2740) of Table 1 were prepared with high zinc plus zirconium contents to obtain diagnostic x-ray opacity; these compositions were much more x-ray opaque than necessary for dental diagnoses.

Composition #2 (K-2715) of Table 1 was subjected to differential thermal analysis at various heating rates, and an exotherm spike was noted at about 890° to about 900° C., depending on the rate of heating. The coefficient of thermal expansion of this formulation before heat treatment was about $3.4 \times 10^{-6}$ per °K. After heat treatment at about 890° to 900° C. for 60 hours, the linear coefficient of thermal expansion was about $4.6 \times 10^{-6}$ per °K. This does not indicate that the coefficient of thermal expansion was reduced by the formation of beta quartz solid solution with this composition and heat treatment. This coefficient of thermal expansion is approximately one-half that of the tooth crown which is approximately $10 \times 10^{-6}$ /°K.

The rationale for the compositions given in mole % as examples in Table 1 is the formulation of compositions in which the modifier oxides of lithium, zinc and magnesium tend to approximate the mole % of aluminum oxide. The purpose of this relationship is to bring aluminum ions into tetrahedral coordination and allow for the growth of beta quartz solid solutions, most of which have extremely low or even negative coefficients of volumetric thermal expansion. The molar proportions are modified somewhat to allow for the separation of nucleating species such as aluminum titinate, which, alone or together with zirconia, yield high temperature quartz ("stuffed beta quartz") by epitaxial nucleation or other mechanisms. The proportions are therefore designed to give microcrystalline glasses with minimal coefficients of thermal expansion and other desirable properties. Other properties include tooth coloration by virtue of the overall compositions as shown in addition to the capability of shade alteration by the use of ionizing radiation of the microcrystalline glass insert. The microcrystalline glass inserts therefore obtain new and useful properties by virtue of extremely small crystal size relative to the wave length of visible light, therefore allowing desired translucency to visible light, and crystallites of the high-temperature quartz configuration, beta-spodumene, beta-eucryptite, and related structures to give low coefficients of thermal expansion to counteract the high thermal expansion of composite restorations not containing an insert. The color of natural teeth is not white, but more closely resembles an amber or yellow-brown tint which is matched in the microcrystalline inserts by the use of compositions containing both cerium oxide and titanium oxide, iron oxide and titanium oxide, and/or iron sulfide, and other means of color generation.

The heat treatment sequence described is only one of a number of variations which will provide for the nucleation and subsequent crystal growth of the desired microcrystalline phases. Preferably, the objects are heat treated to about 30° to 100° C. above the annealing point for times on the order of one hour or more to form crystallization nuclei, and then heated to a temperature between about 750° to 1000° C. for a time sufficient to maximize the crystallization of beta-eucryptite solid solutions, stuffed beta quartz solid solutions, or beta-spodumene solid solutions or keatite. It should be noted that the crystallites of the beta-eucryptite (or "stuffed" beta-quartz) solid solutions are metastable and that heat treatments should not be excessive lest the microcrystalline glass be transformed into one which has higher thermal expansion coefficients, excessive visual opacity and other undesired characteristics.

It should be understood that the foregoing disclosure emphasizes certain specific embodiments of the invention and that all modifications or alternatives equivalent thereto are within the spirit or scope of the invention as set forth in the appended claims.

b) heating the mix to form a liquid;
c) mixing the liquid to homogenize it;
d) cooling the liquid to form cooled objects in assorted shapes and sizes, each of said objects being sized and shaped to full a typical dental cavity as nearly as possible with a single object; and
e) heat treating the cooled objects to obtain inserts having colors and visual translucency substantially within the range of human dentin and enamel, and to separate internal phases.

2. A method as in claim 1, wherein the mix is cooled in step (d) by pressing it into appropriate molds, by drawing and chopping it into small pieces, or by pouring it between cooled rollers synchronized and shaped to form objects of assorted sizes and shapes, each of said objects being sized and shaped to fill a typical dental cavity as nearly as possible with a single object.

3. A method as in claim 1, wherein the objects are heat treated in step (e) so as to produce a microcrystalline glass, and then exposed to ionizing radiation to obtain the desired shade for aesthetic matching of teeth.

4. A method as in claim 1, wherein the objects are heat treated at 30° to 100° C. above the annealing point for times on the order of 1 hour or more to form crystallization nuclei and then heated to a temperature between about 750° to 1,000° C. for a time sufficient to optimize the crystallization of beta-eucryptite solid solutions or keatite solid solutions.

5. A method as in claim 1 wherein the heat treated objects are etched by treating them with one or more solutions comprising a base of sodium fluoride, potassium fluoride, ammonia, $NH_4HF_2$ or $NH_4F$ or with an acid, or both, to remove a surface layer and provide an object of rough-textured surface with increased area.

6. A method as in claim 1 further comprising
(f) applying an adhesion-promoting compound to the insert.

7. A method as in claim 6 wherein the adhesion-promoting compound of step (f) is an organofunctional silane coupling agent, 3-methacryloxypropyltrimethoxy silane.

TABLE 1

EXAMPLES OF GLASS-CERAMIC COMPOSITIONS

| Composition Number (Record Reference) | Composition of Batch (mole %) | | | | | | | | | | |
|---|---|---|---|---|---|---|---|---|---|---|---|
| | $SiO_2$ | $Al_2O_3$ | $Li_2O$ | ZnO | MgO | $TiO_2$ | $ZrO_2$ | $P_2O_5$ | Iron | S | $CeO_2$ |
| 1 (K-2681) | 56 | 20 | | 20 | | | 4 | | | | |
| 2 (K-2715) | 65 | 15.5 | | 15.5 | | | 4 | | | | |
| 3 (K-2740) | 70 | 13 | | 13 | | | 4 | | | | |
| 4 (K-2769) | 70 | 13 | 6 | 7 | | | 4 | | | | |
| 5 (K-2780) | 60 | 18 | 6 | 6 | 6 | | 4 | | | | |
| 6 (K-2781) | 58 | 11 | 6 | 5 | 10 | 6 | 4 | | | | |
| 7 (K-2783) | 59 | 16 | 8 | 8 | 3 | 3 | 3 | | | | |
| 8 (K-2785) | 58 | 21 | 6 | 5 | 6 | 4 | | | | | |
| 9 | 56 | 21 | 6 | 5 | 6 | 5.9 | | | 0.1 $Fe_2O_3$ | | |
| 10 | 56.73 | 15 | 15 | | 6 | | 4 | 3 | 0.2 $Fe(C_2O_4).2H_2O$ | 0.07 | |
| 11 | 42 | 28 | 7 | 7 | 7 | 7 | | | | | 2 |

What is claimed is:

1. A method for repairing a dental cavity comprising filling the cavity with unhardened composite material or resin; selecting, from an array of assorted pre-formed dental inserts sized from about 0.5 to about 10 mm and shaped to fit typical dental cavities, an insert sized and shaped so as to fill the cavity as nearly as possible; pressing the insert into the unhardened composite or resin; removing excess extruded composite or resin; curing the composite material or resin; and contouring the surface of the insert and hardened composite material as needed; wherein said insert comprises a microcrystalline glass having a coefficient of thermal expansion less than about $5 \times 10^{-6}/°K$ and containing one or more phases of beta-quartz solid solution, beta-spodumene solid solution, beta-eucryptite solid solution, stuffed beta-quartz and keatite; and wherein said insert is prepared by a method comprising:

a) preparing a mix consisting essentially of about 56 to about 60 percent $SiO_2$; about 16 to about 21 percent $Al_2O_3$; about 6 to about 8 percent $Li_2O$; about 5 to about 20 percent ZnO; about 3 to about 6 percent MgO; about 0 to about 6 percent $TiO_2$; about 0 to about 4 percent $ZrO_2$; about 0 to about 3 percent $P_2O_5$; about 0 to about 0.2 percent $Fe_2O_3$; and about 0 to about 2 percent $CeO_2$; to provide an X-ray opacity, shade, and visual translucency substantially within the range of human dentin and enamel upon treatment as specified hereinafter;